United States Patent [19]

Murphy et al.

[11] Patent Number: 4,904,184
[45] Date of Patent: Feb. 27, 1990

[54] PERIODONTAL PROBE INSTRUMENT

[76] Inventors: Gordon J. Murphy, 638 Garden Court; Robert J. Ceisel, 1450 Ammer Rd., both of Glenview, Ill. 60025

[21] Appl. No.: 296,989

[22] Filed: Jan. 17, 1989

[51] Int. Cl.$^4$ .............................................. A61C 19/04
[52] U.S. Cl. ........................................ 433/72; 128/776
[58] Field of Search ............................. 433/72, 75, 32; 128/776, 777; 33/513, 514

[56] References Cited

U.S. PATENT DOCUMENTS

| | | | |
|---|---|---|---|
| 3,058,225 | 10/1962 | Ward | 128/776 |
| 3,943,914 | 3/1976 | Grenfell et al. | 433/72 |
| 4,203,223 | 5/1980 | Lautenschlager et al. | 433/75 |
| 4,340,069 | 7/1982 | Yeaple | 433/72 |
| 4,665,621 | 5/1987 | Ackerman et al. | 433/32 |
| 4,677,756 | 7/1987 | Simon et al. | 128/776 |
| 4,764,114 | 8/1988 | Jeffcoat et al. | 128/776 |
| 4,791,940 | 12/1988 | Hirschfeld et al. | 433/72 |

*Primary Examiner*—John J. Wilson
*Attorney, Agent, or Firm*—Davis Chin

[57] ABSTRACT

A periodontal probe instrument for measuring the depth of a periodontal pocket in the gingiva adjacent a tooth includes a probe handle member in which a displacement sensor and a probe element are mounted. The probe element includes an external end and is disposed adjacent and parallel to the displacement sensor. A tip of the displacement sensor is aligned with the external end of the probe element in a first reference position. A pressure transducer is mounted in the handle member for generating a first output signal indicative of the magnitude of the force applied. A displacement transducer is mounted in the handle member for constantly encoding the displacement of the tip of the displacement sensor as it is moved from the first position to a second position to generate a second output signal indicative of the depth of the periodontal pocket. A comparator circuit is provided for generating a logic signal only when the first output signal is in the range between a low threshold signal and a high threshold signal. An indicator is responsive to the logic signal to produce an indication to generate an actuation signal. In response to the indication to generate an actuation signal, a switch is operated to cause a computer to read the second output signal indicative of the depth of the periodontal pocket.

18 Claims, 2 Drawing Sheets

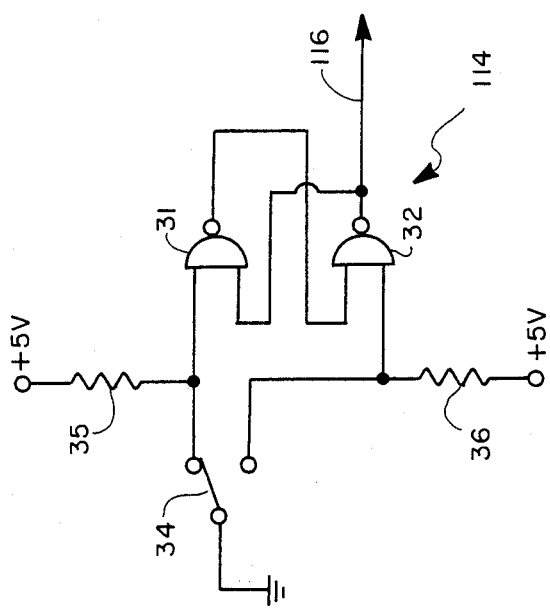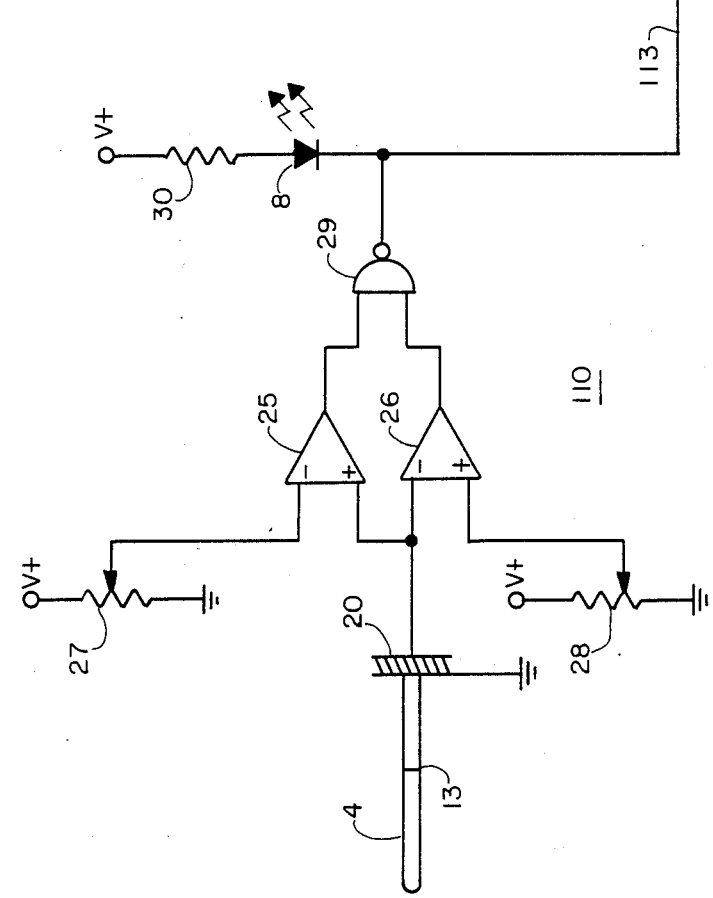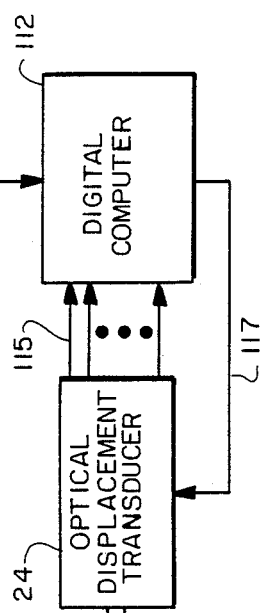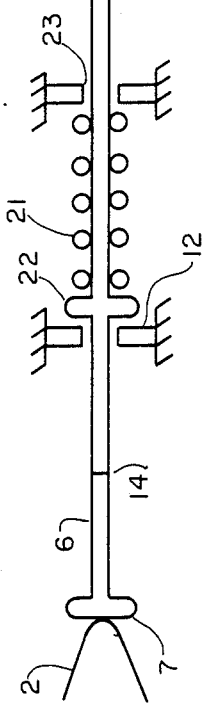
FIG. 2
FIG. 3

PERIODONTAL PROBE INSTRUMENT

BACKGROUND OF THE INVENTION

1. Field of the Invention

The present invention relates generally to periodontics and more particularly it relates to a periodontal probe instrument used to measure the depth of the gingival sulcus and periodontal pockets.

2. Description of the Prior Art

Chronic periodontal disease is an inflammatory disease typically induced by plaque formation. As a result of progressive bone loss around the teeth as a consequence of the disease, the increased sulcus depths in the gums create periodontal pockets. These pockets are indicative of the progression of the disease. To diagnose and treat periodontal disease adequately, it is necessary to monitor the current activity of the disease as well as to evaluate past periodontal destruction. To do that requires that the depths of the gingival sulcus and any periodontal pockets that exist be determined accurately.

Pocket depths are now commonly measured by a periodontal probe that has a thin metal tip that is scored with calibration marks. The probe is inserted into the sulcus between a tooth and the gingiva and advanced until resistance is felt, which indicates that the bottom of the pocket has been reached. A depth reading is then obtained by observing visually the calibration mark that is closest to the top of the gingival margin. Six depth readings are taken around each tooth at prescribed locations, as standard practice. Each of the six readings is recorded. Frequently this recording is done by verbal reporting of the depth to an assistant, who writes it by hand on a dental chart.

Clearly, the use of such a conventional periodontal probe is a time-consuming and hence expensive procedure. Moreover, the depths of the periodontal pockets recorded during such a procedure are not always very accurate. Human error results from the need to interpolate between the calibration marks on the probe, as well as from variations in the pressure of the probe against the bottom of the periodontal pocket at the instant that the depth reading is taken. Additional error sometimes arises from the verbal communciation of the measured values and the manual writing of those values on the record.

A patent search produced the following seven patents in which a periodontal probe with a depth measurement structure is disclosed:

| U.S. Pat. No. | Dated | Patentee |
| --- | --- | --- |
| 3,058,225 | Oct. 16, 1962 | Ward |
| 3,943,914 | Mar. 16, 1976 | Greniell et al. |
| 4,250,895 | Feb. 17, 1981 | Lees |
| 4,340,069 | Jul. 20, 1982 | Yeaple |
| 4,665,621 | May 19, 1987 | Ackerman et al. |
| 4,677,756 | Jul. 7, 1987 | Simon et al. |
| 4,708,647 | Nov. 24, 1987 | Pippin et al. |

Independently, references to periodntal probes were located in U.S. Pat. No. 4,203,223 issued May 20, 1980 to Lautenschlager et al. and a paper entitled "Computerized Periodontal Probe with Adjustable Pressure", written by E. Sild et al., which was published on pp. 53-62 of The International Journal of Periodontics and Restorative Dentistry for April, 1987.

SUMMARY OF THE INVENTION

The object of this invention is a periodontal probe with controllable pressure that indicates the depth of a periodontal pocket accurately and automatically. The depth of the pocket is converted within the probe to a digital signal that can be transmitted automatically to a digital computer for recording, in response to a signal generated within the probe when the correct pressure is applied to the probe via the handle of the probe or in response to the activation of a switch on the handle of the probe by the user of the probe when the measured pressure is acceptable for taking a reading and the probe is seen to be properly positioned in the periodontal pocket. The use of a digital output signal from the probe in preference to an analog output signal results in an improved signal-to-noise ratio and consequently to improved accuracy in the measurement of the depth of the periodontal pocket. An analog signal, obtained from a potentiometer, may be supplied instead of the digital signal, however, to allow a reduction in the size of the probe, if that is desirable. In that case, the conversion of the analog signal to a digital signal is effected in an external analog-to-digital converter.

The pressure is provided by means of an elastic restraint that introduces no significant displacement error into the measurement of pocket depth, and the interface to a digital computer allows the use of various computer programs to process stored data on the depths of periodontal pockets in a selected group of patients as well as the depths of the pockets in a given patient.

In one embodiment of this invention, the pressure exerted by the probe is measured by a piezo-electric sensor in a bridge type of strain gauge, but other forms of strain gauge may also be used. A characteristic of strain gauges that is important for use in a periodontal probe is that they require no significant displacement of the tip of the probe to generate a pressure signal. When the pressure is within a predetermined range of values, a light-emitting diode indicates that the depth of the pocket may be read. The depth of the pocket is measured by a depth sensor, which consists of a steel wire within a tube. The tip of the steel wire is broadened to prevent puncturing of the gingiva. The depth sensor is mounted on the body of the instrument in such a way that the displacement of the tip of the steel wire from the tip of the probe indicates the depth of the periodontal pocket if the tip of the steel wire rests on the gingival margin and the tip of the probe rests at the bottom of the pocket. The steel wire is constantly urged by a spring in the tube toward a position in which the tip of the steel wire is aligned with the tip of the probe.

With the tip of the steel wire resting on the gingival margin, the handle of the instrument is pushed in such a direction as to tend to move the probe into the periodontal pocket. As a result, the steel wire is forced into the tube, compressing the spring. The displacement of the tip of the wire from its initial extension from the tube is constantly monitored by a displacement transducer. Said displacement transducer may consist of a combination of a potentiometer and an analog-to-digital converter or of a wire-brush digital displacement encoder or of an optical displacement encoder. Because the tip of the wire remains at all times at rest on the gingival margin, the signal obtained from the displacement transducer indicates the depth to which the probe has entered the pocket. Because the spring serves only to hold the steel wire in position against the gingiva and contributes in no other way to the reading, ordinary problems of spring calibration and changes in spring characteristics over time are irrelevant.

When the probe reaches the bottom of the pocket, resistance to further motion of the probe is provided by the bottom of the pocket. The amount of this resistance is measured by the strain gauge. The output of the strain gauge is transmitted to a range circuit. When the electrical output of the range circuit falls within a predetermined range, indicative of appropriate pressure for a reading of pocket depth, a light-emitting diode is activated. If the operator of the instrument is satisfied with the positioning of the probe and the depth sensor at that time, he activates a switch that causes the signal provided by the displacement transducer to be entered into a digital computer, via a program in the computer that operates to store the value of the pocket depth for processing at a later time.

In another embodiment, the signal provided by the displacement transducer is automatically entered into the digital computer when the electrical output of the range circuit enters the predetermined range of appropriate pressure for a reading of pocket depth.

BRIEF DESCRIPTION OF THE DRAWINGS

The above and other advantages and features of the invention will be apparent to those skilled in the art from the following description taken in conjunction with the accompanying drawings, in which:

FIG. 2 is a diagram of the system for obtaining a reading of the depth of the pocket at an acceptable probe pressure from the probe assembly; and FIG. 3 is a schematic circuit diagram of a debouncing circuit for use with the system of FIG. 2 in an alternate embodiment.

DESCRIPTION OF THE PREFERRED EMBODIMENTS

Figure 1:
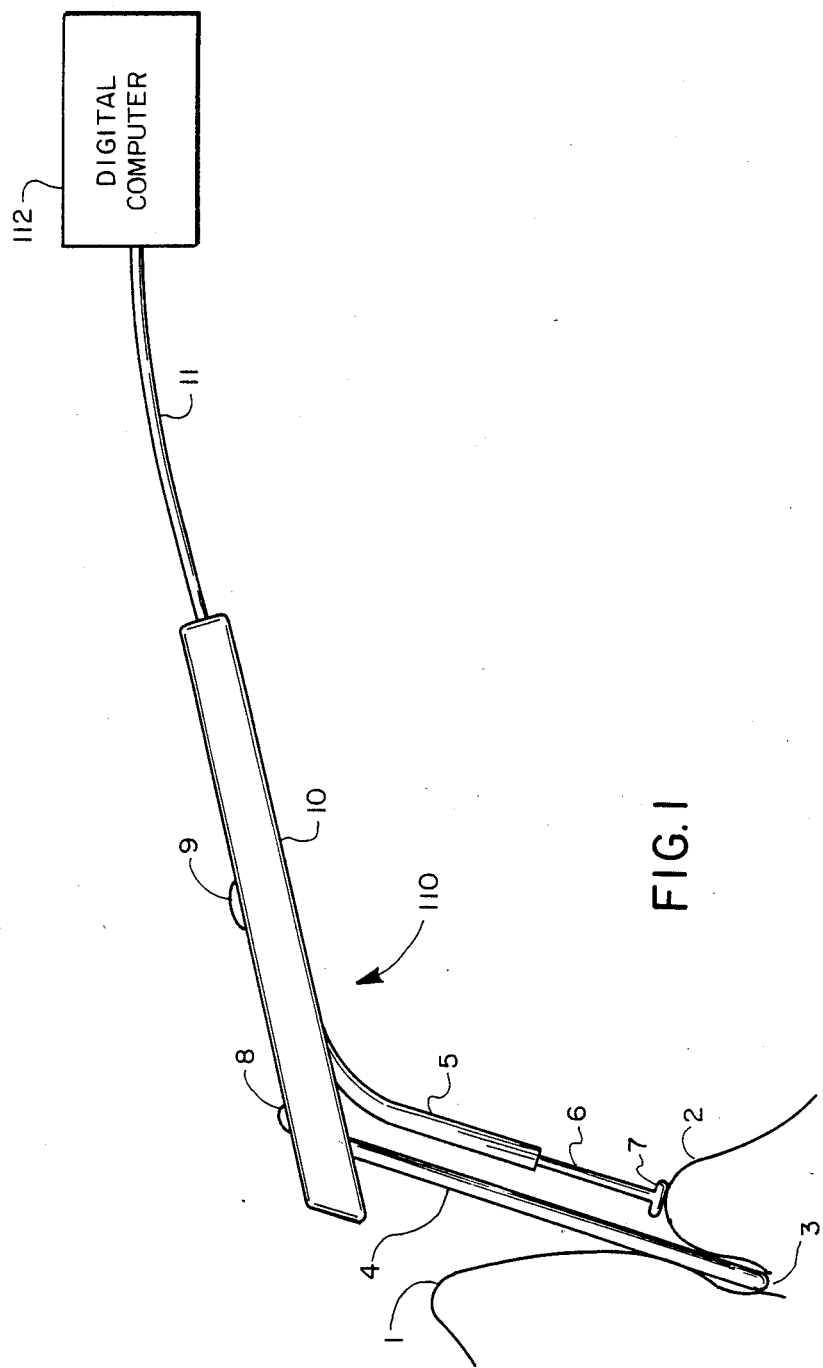
FIG. 1 is a drawing of the probe assembly, with the probe in position in a peridodontal pocket and the depth sensor in position on the gingival margin.

With reference to FIG. 1, a preferred embodiment of the novel periodontal probe instrument is shown in diagrammatic form and designated generally by reference numeral 110. A probe 4 is mounted in a handle 10 in such a manner that the probe is free to slide a short distance further or less far into the handle. Pressure applied to the external end of the probe 4 tends to cause the probe to move further into the handle 10. This motion of the probe 4 is impeded, however, by a pressure sensor formed preferably of a piezo-electric sensor in a type of strain gauge and mounted within the handle, which permits only a minute displacement of the probe, sufficient to produce an analog electrical output signal from the pressure sensor. The electrical output signal indicates the magnitude of the force applied to the external end of the probe 4.

Also mounted in the handle 10 is a displacement sensor comprising a movable flexible wire 6, terminated externally in a broadened tip 7 and terminated within the handle 10 in a displacement transducer; a sleeve 5 in which the movable wire can slide so that the broadened tip of the movable flexible wire can be moved or retracted from a reference position, determined by a first mechanical stop, in which the broadened tip is aligned with the external end of the probe 4 to a second position, determined by a second mechanical stop; and a spring contained within the sleeve. The function of this spring is to supply a light force, the magnitude of which is of no importance, to urge the wire to return to its reference position.

In normal use of the periodontal probe instrument, the probe 4 is placed next to a tooth 1 with the broadened tip 7 of the displacement sensor resting on the gingival margin 2. A force is then applied manually to the handle 10 to urge the probe 4 into the periodontal pocket until the external end of the probe presses against the bottom 3 of the periodontal pocket. The force applied to the handle 10 is then adjusted until the pressure sensor indicates that the pressure exerted by the probe against the bottom of the periodontal pocket is within a predetermined acceptable range. In response to the output of the pressure sensor, a light-emitting diode 8 mounted in the handle 10 is then activated.

The displacement of the broadened tip 7 of the displacement sensor is constantly being encoded by the displacement transducer. When the light-emitting diode 8 is activated, therefore, the digital output signal provided by the displacement transducer indicates the depth of the periodontal pocket with acceptable accuracy. In response to the activation of the light-emitting diode, the operator of the periodontal probe momentarily presses a button 9 mounted in the handle 10, thus activating a switch mounted also in the handle. In response to the activation of the switch, the digital output signal provided by the displacement transducer is transmitted over a cable 11 to a digital computer for processing. Alternatively, instead of manually actuating a switch mounted in the handle 10, the operator of the probe may use a foot-operated switch connected in place of the switch mounted in the handle 10.

Although in FIG. 1 the probe 4 is shown directly ahead of the movable flexible wire 6, it will be apparent that for ease of access to different locations around the teeth of the patient, one or more alternative arrangements of the probe 4 and the movable flexible wire 6 may be desired. Accordingly, periodontal probes of the kind disclosed herein may be built with the probe 4 to the left of the flexible movable wire 6, for example, or to the right thereof. A further improvement to the periodontal probe consists of mounting the probe 4 and the pressure sensor to which it is connected in a ring assembly, with detents, that can be rotated about the flexible movable wire 6 to position the probe 4 at any one of a number of locations relative to the flexible movable wire 6. In such an arrangement, the electrical connections to the pressure sensor may be flexible electrically conducting wires if the rotation of the ring assembly is constrained to an angle of less than 360 degrees, for example; alternatively, the electrical connections to the ring assembly may consist of slip rings to facilitate continuous rotation of the ring assembly.

With reference to FIG. 2, the operation of the periodontal probe is shown in greater detail. As the probe 4 is inserted into the periodontal pocket with the broadened end 7 of the movable flexible wire 6 resting on the gingival margin 2, the movable flexible wire compresses a spring 21 restrained at one end by a mechanical stop 23 in the handle 10 shown in FIG. 1 and at the other end by a mechanical stop 22 on the movable flexible wire 6. The displacement of the broadened end 7 of the movable flexible wire 6 from its reference position in alignment with the external end of the probe 4 is encoded by a displacement transducer 24 formed preferably of an optical displacement encoder and mounted in the handle shown in FIG. 1. When the probe 4 is removed fro the periodontal pocket, the broadened end 7 of the movable flexible wire 6 is returned to its reference position by the action of the spring 21 and is prevented from moving any farther by contact of the mechanical stop 22 on the movable flexible wire with another mechanical stop 12 mounted on the handle 10 shown in FIG. 1.

In response to pressure applied to the external end of the probe 4, a strain gauge 20 generates an analog electrical output signal, which is applied to the non-inverting input terminal of a first comparator 25 and to the inverting input terminal of a second comparator 26. A first low threshold voltage, obtained from a first potentiometer 27 supplied with a positive reference voltage V+, is applied to the inverting input terminal of the first comparator, and a second high threshold voltage, obtained from a second potentiometer 28 supplied with the same positive reference voltage, is applied to the non-inverting input terminal of the second comparator. The potentiometers 27 and 28 are adjusted so that the second threshold voltage is larger than the first threshold voltage and so that when the pressure applied to the external end of the probe 4 is within a predetermined acceptable range, the electrical output signal of the strain gauge 20 is larger than the first threshold voltage and less than the second threshold voltage.

Consequently, when the pressure applied to the external end of the probe 4 is less than the minimum acceptable value the output voltage of the first comparator 25 is low and the output voltage of the second voltage comparator 26 is high. In response to these output voltages of the comparators, the TTL NAND gate 29 supplies an output voltage that is high, and the current in the light-emitting diode 8 is negligible. Accordingly, no discernible light is emitted by the light-emitting diode. When the pressure applied to the external end of the probe 4 is greater than the maximum acceptable value the output voltage of the first comparator 25 is high and the output voltage of the second comparator 26 is low. In response to these output voltages of the comparators, the TTL NAND gate 29 also supplies an output voltage that is high, and the current in the light-emitting diode 8 is negligible. Again no discernible light is emitted by the light-emitting diode. When the pressure applied to the external end of the probe 4 is on the acceptable range of values, however, the output voltage of the first comparator 25 and the output voltage of the second comparator 26 are both high, and the response of the TTL NAND gate 29 to these output voltages of the comparators is to provide an output voltage of the NAND gate 29 that is low. In response to the low output voltage of the TTL NAND gate 29, the current in the light-emitting diode 8 becomes large enough to cause the light-emitting diode to emit a clearly visible amount of light. The purpose of the resistor 30 is to limit the current.

The logic signal defined by the output voltage of the TTL NAND gate 29 is transmitted automatically to the computer 112 via the line 113. When the logic signal makes a high-to-low transition, the computer responds to the logic signal by reading and storing the digital output signal 115 of the displacement transducer 24 by means of a control signal on line 117.

Referring now to FIG. 3, there is shown a schematic circuit diagram of a debouncing circuit 114 with a manually operated switch 34 for use with the system of FIG. 2 in an alternate embodiment. In response to the light signal emitted by the light-emitting diode 8, the operator of the periodontal probe momentarily presses the button 9 shown in FIG. 1 mounted on the handle 10 shown in FIG. 1, thus momentarily activating the manually operated momentary-contact switch 34 shown in FIG. 3. Alternatively, instead of actuating the switch 34 shown in FIG. 3, the operator of the probe instrument 110 may use a foot-operated momentary-contact switch connected in place of the switch 34 mounted in the handle 10. Regardless of the location of the momentary-contact switch used, the momentary-contact switch is debounced by the debouncing circuit 114 consisting of two TTL NAND gates 31 and 32 and two pull-up resistors 35 and 36. As a result, the output voltage of the debouncing circuit on line 116 defining an activation sinal, which is normally low, becomes high during the interval of time on which the momentary-contact switch 34 is held down and returns to its normal low value when the momentary-contact switch is released. The output voltage of the debouncing circuit is transmitted to the computer 112 in the cable 11 shown in FIG. 1. The computer responds to the high value of the activation signal on the line 116 of the debouncing circuit by reading the digital output signal of the displacement transducer 24 mounted in the handle 10 shown in FIG. 1, which indicates the depth of the periodontal pocket.

If desired, an acoustical tone generator may be used instead of or in addition to the light-emitting diode 8 to indicate that a reading of pocket depth may be taken.

To facilitate sterilization of the portions of the periodontal probe that contact the patient, the outermost portion of the probe 4 can be removed from the remainder of the probe at a location 13 close to the handle 10 shown in FIG. 1, and the outermost portion of the movable flexible wire 6 can be removed from the remainder of the movable flexible wire at a location 14 close to the external end of the sleeve 5 when the broadened tip 7 of the movable flexible wire is in its reference position. Removability of the outermost portions of the probe 4 and the movable flexible wire 6 may be achieved by the provision of threads to permit the screwing of these outermost portions to their respective mating pieces and the unscrewing of the outermost portions therefrom. Alternatively, the outermost portion of the probe 4 may be attached to the remainder of the probe by means of a press fit, and the outermost portion of the movable flexible wire 6 may be attached to the remainder of the movable flexible wire by means of a press fit for ease and speed of removal and replacement.

The comparators 25 and 26, the TTL NAND gates 29, 31, and 32, and the optical displacement encoder 24 are supplied with five volts in the normal manner to enable their operation.

It will be apparent to one skilled in the art that an improvement can be made by the addition of two optional light-emitting diodes with current-limiting resistors, connected so as to indicate when the output voltage of the first comparator 25 is low, to signal that the probe 4 must be pressed further into the periodontal pocket, and to indicate when the output voltage of the second comparator 26 is low, to signal that the pressure of the probe 4 against the bottom of the periodontal pocket must be reduced.

The periodontal probe invention described herein is not disclosed in any of the patents listed above, nor in the referenced paper written by Sild et al. The publication by Sild et al. appears to contain the disclosure most closely related to the invention, which may be viewed as an improvement on the probe disclosed in that publication. The differences in the probe of the invention with respect to the probe disclosed in the publication by Sild et al. are as follows:

1. The pressure of the probe against the gingival tissue is provided by a strain gauge instead of by a metal spring.

2. The occurrence of the correct value of pressure is indicated by a light signal, which is either on or off, instead of by displacement, which varies continuously over a finite range and is relatively difficult to interpret.

3. The depth sensor engages the gingival margin automatically and under spring pressure, instead of requiring manual movement.

4. In one embodiment, the depth of the pocket is measured by means of a digital transducer, instead of by a potentiometer that produces analog data which are then converted to digital data.

The arrangement of a wire-type depth sensor and an adjacent parallel probe element is not disclosed in any of the patents noted in the search, and none of said patents discloses a wire-type depth sensor spring-pressed against the gingiva. In addition, the use of a light signal to indicate the occurrence of the appropriate pressure for reading pocket depth is not disclosed in any of the prior art known to exist, nor is the use of the electrical signal that actuates the light signal to cause automatic reading of the depth of the pocket without requiring the operator of the probe to actuate a switch.

While only particular embodiments of the invention have been described and illustrated, it is apparent that modifications may be made therein. It is the object of the inventors in the appended claims to cover all such modifications as may fall within the true scope and spirit of the invention.

What is claimed is:

1. A periodontal probe instrument for measuring the depth of a periodontal pocket in the gingiva adjacent a tooth, said instrument comprising:

a probe handle member;

a displacement sensor being movably mounted within a sleeve which is connected to said probe handle member, said displacement sensor terminating externally of said handle member in a tip;

a probe element including an external end and being also mounted in said handle member, said probe element being disposed adjacent and parallel to said displacement sensor;

said tip of said displacement sensor being aligned with said external end of said probe element in a first reference position;

pressure transducer means mounted in said handle member and being responsive to a force applied to said external end of said probe element for generating a first output signal indicative of the magnitude of the force;

said probe element being inserted into the periodontal pocket until the external end thereof contacts the bottom of the pocket as the tip of said displacement sensor is resting on the gingival margin of the tooth, said tip being retracted in said sleeve from the first position to a second position when the external end of said probe element is contacting the bottom of the pocket;

displacement transducer means mounted in said handle member for constantly encoding the displacement of said tip as it is moved from the first position to the second position to generate a second output signal indicative of the depth of the periodontal pocket;

comparator means responsive to said first output signal indicative of the magnitude of the force, a low threshold signal, and a high threshold signal for generating a logic signal only when said first output signal is in the range between said low and high threshold signals;

indicating means responsive to said logic signal to produce an indication to generate an actuation signal; and activating means including a switch which is operated when the indication is produced for generating an actuation signal to cause a computer to read the second output signal indicative of the depth of the periodontal pocket.

2. A probe instrument as claimed in claim 1, wherein said displacement sensor comprises a movable flexible wire which is biased against a mechanical stop by a spring to the first reference position.

3. A probe instrument as claimed in claim 1, wherein said pressure transducer means comprises a piezo-electric sensor in a type of strain gauge.

4. A probe instrument as claimed in claim 1, wherein said displacement transducer means comprises an optical displacement encoder.

5. A probe instrument as claimed in claim 1, wherein said comparator means comprises a first comparator having a non-inverting input, an inverting input, and an output; a second comparator having a non-inverting input, an inverting input, and an output; and a NAND logic gate, said non-inverting input of said first comparator and said inverting input of said second comparator being coupled to receive said first output signal indicative of the magnitude of the force, said inverting input of said first comparator being coupled to receive said low threshold signal, said non-inverting input of said second comparator being coupled to receive said high threshold signal, and said logic gate having a first input connected to the output of said first comparator, a second input connected to the output of said second comparator, and an output for producing the logic signal.

6. A probe instrument as claimed in claim 5, wherein said low threshold signal is a voltage produced by a first potentiometer coupled to a reference voltage.

7. A probe instrument as claimed in claim 6, wherein said high threshold signal is a voltage produced by a second potentiometer coupled to the reference voltage.

8. A probe instrument as claimed in claim 1, wherein said indicating means comprises a light-emitting diode.

9. A probe instrument as claimed in claim 1, wherein said activation means further includes a debouncing circuit formed of a pair of NAND logic gates and two pull-up resistors, one of the outputs of said pair of NAND logic gates making a low-to-high transition to define the actuation signal upon depression of said manually operated switch.

10. A periodontal probe instrument for measuring the depth of a pepriodontal pocket in the gingiva adjacent a tooth, said instrument comprising:

a probe handle member;

a displacement sensor being movably mounted within a sleeve which is connected to said probe handle member, said displacement sensor terminating externally of said handle member in a tip;

a probe element including an external end and being also mounted in said handle member, said probe element being disposed adjacent and parallel to said displacement sensor;

said tip of said displacement sensor being aligned with said external end of said probe element in a first reference position;

pressure transducer means mounted in said handle member and being responsive to a force applied to said external end of said probe element for generating an analog output signal indicative of the magnitude of the force;

said probe element being inserted into the periodontal pocket until the external end thereof contacts the bottom of the pocket as the tip of said displacement sensor is resting on the gingival margin of the tooth, said tip being retracted in said sleeve from the first position to a second position when the external end of said probe element is contacting the bottom of the pocket;

displacement transducer means mounted in said handle member for constantly encoding the displacement of said tip as it is moved from the first position to the second position to generate a digital output signal indicative of the depth of the periodontal pocket;

comparator means responsive to said analog output signal indicative of the magnitude of the force, a low threshold signal, and a high threshold signal for generating a logic signal only when said first output signal is in the range between said low and high threshold signals;

indicating means responsive to said logic signal to produce an indication to generate an actuation signal; and digital processing means also responsive to said logic signal for automatically reading the digital output signal indicative of the depth of the periodontal pocket.

11. A probe instrument as claimed in claim 10, wherein said displacement sensor comprises a movable flexible wire which is biased against a mechanical stop by a spring to the first reference position.

12. A probe instrument as claimed in claim 10, wherein said pressure transducer means comprises a piezo-electric sensor in a type of strain gauge.

13. A probe instrument as claimed in claim 10, wherein said displacement transducer means comprises an optical displacement encoder.

14. A probe instrument as claimed in claim 10, wherein said comparator means comprises a first comparator having a non-inverting input, an inverting input, and an output; a second comparator having a non-inverting input, an inverting input, and an output; and a NAND logic gate, said non-inverting input of said first comparator and said inverting input of said second comparator being coupled to receive said analog output signal, said inverting input of said first comparator being coupled to receive said low threshold signal, said non-inverting input of said second comparator being coupled to receive said high threshold signal, and said logic gate having a first input connected to the output of said first comparator, a second input connected to the output of said second comparator, and an output for producing the logic signal.

15. A probe instrument as claimed in claim 14, wherein said low threshold signal is a voltage produced by a first potentiometer coupled to a reference voltage.

16. A probe instrument as claimed in claim 15, wherein said high threshold signal is a voltage produced by a second potentiometer coupled to the reference voltage.

17. A probe instrument as claimed in claim 10, wherein said indicating means comprises a light-emitting diode.

18. A probe instrument as claimed in claim 10, wherein said digital processing means comprises a computer.

* * * * *